(12) United States Patent
Ravichandran et al.

(10) Patent No.: US 6,834,553 B2
(45) Date of Patent: Dec. 28, 2004

(54) PROOF TESTING CAPSTANS FOR REDUCING SHEAR AND FIBER COATING DEFORMATION

(75) Inventors: Manivannan Ravichandran, Wilmington, NC (US); Kenneth W. Roberts, Wilmington, NC (US); Johnnie E. Watson, Hampstead, NC (US)

(73) Assignee: Corning Incorporated, Corning, NY (US)

( * ) Notice: Subject to any disclaimer, the term of this patent is extended or adjusted under 35 U.S.C. 154(b) by 89 days.

(21) Appl. No.: 10/203,738

(22) PCT Filed: Feb. 6, 2001

(86) PCT No.: PCT/US01/03870

§ 371 (c)(1),
(2), (4) Date: Aug. 13, 2002

(87) PCT Pub. No.: WO01/71304

PCT Pub. Date: Sep. 27, 2001

(65) Prior Publication Data

US 2003/0011759 A1 Jan. 16, 2003

Related U.S. Application Data

(60) Provisional application No. 60/190,860, filed on Mar. 20, 2000.

(51) Int. Cl.[7] ................................................ G01N 3/08
(52) U.S. Cl. .............................. 73/829; 73/828; 73/830
(58) Field of Search ........................... 73/827–837, 788, 73/826

(56) References Cited

U.S. PATENT DOCUMENTS

| 4,148,218 A | * | 4/1979 | Knowles et al. | ............... 73/829 |
|---|---|---|---|---|
| 4,286,469 A | * | 9/1981 | Trias | ............................ 73/829 |
| 4,393,701 A | * | 7/1983 | Lawson | ........................ 73/160 |
| 4,410,344 A | * | 10/1983 | Iyengar | ........................ 65/382 |
| 4,601,208 A | | 7/1986 | McKay et al. | ................. 73/829 |
| 4,825,702 A | * | 5/1989 | Cizek | ........................... 73/828 |
| 5,647,884 A | * | 7/1997 | Overton et al. | ................ 65/533 |

FOREIGN PATENT DOCUMENTS

| FR | 0 785 173 | 7/1997 | ........... C03B/37/03 |
|---|---|---|---|
| WO | WO 01/51911 | 7/2001 | ............. G01N/3/08 |

OTHER PUBLICATIONS

Patent Abstracts of Japan, JP 60179625, Feb. 27, 1984, T. Yoshimitsu; Nippon Telegr & Teleph Corp.

* cited by examiner

*Primary Examiner*—Edward Lefrowitz
*Assistant Examiner*—Alandra Ellington
(74) *Attorney, Agent, or Firm*—Randall S. Wayland; William J. Chervenak

(57) ABSTRACT

An apparatus for proof testing an optical waveguide fiber includes a first capstan defining a first outer diameter and a continuous first capstan belt under tension and in contact with the first outer diameter of the first capstan. The contact between the first capstan belt and the first capstan defining a first arc of contact, and the first capstan belt defining a first width, a first thickness and a first length. The apparatus further includes a second capstan defining a second outer diameter and a continuous second capstan belt under tension and in contact with the outer diameter of the second capstan. The contact between the second capstan belt and the second capstan defining a second arc of contact, second capstan belt defining a second width, second thickness and a second belt length. The first arc of contact being equal to or greater than about 105° and the second arc of contact being at least 20° greater than the first arc of contact.

39 Claims, 3 Drawing Sheets

PROOF TESTING CAPSTANS FOR REDUCING SHEAR AND FIBER COATING DEFORMATION

This application claims the benefit of and priority to U.S. Provisional Patent Application No. 60/190,860, filed Mar. 20, 2000 and PCT Application Number PCT/US01/03870, filed Feb. 6, 2001.

BACKGROUND OF THE INVENTION

1. Field of the Invention

The present invention relates to capstans for proof testing, and in particular to capstans for proof testing that reduce shear imposed on an optical waveguide fiber and for reducing deformation of the coating of the optical waveguide fiber during the proof testing process.

2. Technical Background

Capstan assemblies as used in the manufacture of optical waveguide fibers are typically used to draw the optical fibers from glass blanks that are mounted within draw towers, and/or for proof testing of the optical fiber, also known as fiber screening. For consistency, the term proof testing will be used herein.

Capstan assemblies typically include a capstan pulley and a capstan belt between which the optical fiber is positioned. As the capstan pulley is rotated, the friction generated between the capstan pulley, the optical fiber and the capstan belt pulls or draws the optical fiber from the associated glass blank through a series of related operations such as coating and sizing steps. When used in tandem, capstan assemblies can also be used to test the proof strength of the optical fiber by placing a tensile stress thereon.

While stressing the fiber is necessary to test for proof strength, the shear forces imposed on the coating during the process of applying the required proof stress to the fiber should be limited to avoid the negative effect of damaging the coating.

When used for proof testing, capstans typically have some region in the arc of contact of the fiber with the capstan pulley where the optical fiber is slipping relative to the capstan, thereby defining an arc of slip. The region about the capstan pulley that the optical fiber is not slipping is defined as the arc of adhesion. This slip is actually desirable to minimize shear, as shear is reduced, or its increase is limited, once slip occurs. Therefore, earlier slip results in less shear. For a given set of capstan pulley/belt materials, the slip is a function of the lateral load on the fiber due to the belt and the fiber tension and varies inversely thereto.

In the prior art, the lateral load on a fiber is reduced by reducing the belt tension. This solution poses some practical problems, including 1) reducing belt tension to the point that no "arc of adhesion" occurs between the fiber and the capstan, thus resulting in catastrophic slip and compromising proof testing of the optical fiber, and 2) belt tracking (i.e., its propensity for side-to-side motion) as well as lateral fixity of the fiber (i.e., how well the fiber position beneath the belt is maintained against side-to-side motion).

At the other extreme, increasing the lateral load on the optical fiber, thereby reducing slip, by increasing the belt tension poses additional problems. These include coating damage, which is manifested as cohesive failure at or near the coating/glass interface. More specifically, the lateral load as supported by the fiber can cause permanent or irrecoverable deformation of the coating surrounding the optical fiber.

A capstan assembly that provides sufficient tension during drawing and/or proof testing of an optical fiber while reducing unwanted shear on the optical fiber and deformation of the associated fiber coating would be advantageous for ensuring proof strength and coating integrity.

SUMMARY OF THE INVENTION

One aspect of the present invention is to provide an apparatus for proof testing an optical waveguide fiber that includes a first capstan pulley defining a first outer diameter and a continuous first capstan belt under tension and in contact with the first outer diameter of the first capstan pulley, wherein the contact between the first capstan belt and the first capstan pulley define a first arc of contact, and the first capstan belt defines a first belt width, a first belt thickness and a first belt length. The apparatus further includes a second capstan pulley defining a second outer diameter and a continuous capstan belt under tension and in contact with the outer diameter of the second capstan pulley, wherein the contact between the second capstan belt and the second capstan pulley defines a second arc of contact, the second capstan belt defines a second belt width, a second belt thickness and a second belt length. The first arc of contact is preferably equal to or greater than about 105° and the second arc of contact is at least 20° greater than the first arc of contact. The first arc of contact can be as low as 90°.

Another aspect of the present invention is to provide an apparatus for proof testing an optical waveguide fiber that includes a first capstan pulley defining a first outer diameter and a continuous capstan belt under tension and in contact with the first outer diameter of the first capstan pulley, wherein the contact between the first capstan belt and the first capstan pulley defines a first arc of contact, and the first capstan belt defines a first belt width, a first belt thickness and a first belt length. The apparatus further includes a second capstan pulley defining a second outer diameter and a continuous second capstan belt under tension and in contact with the outer diameter of the second capstan pulley, wherein the contact between the second capstan belt and the second capstan pulley defines a second arc of contact, and the second capstan belt defines a second belt width, a second belt thickness and a second belt length. The first width of the first capstan belt and the second width of the second capstan belt each have a lateral modulus of elasticity, and the first length of the first capstan belt and the second length of the second capstan belt each have a longitudinal modulus of elasticity, and the lateral modulus of elasticity of each belt is between about ⅕ and about ⅙ the longitudinal modulus of elasticity of each belt.

Yet another aspect of the present invention is to provide an apparatus for proof testing an optical fiber that includes a first capstan pulley defining a first outer diameter and a continuous first capstan belt under tension and in contact with the first outer diameter of the first capstan pulley, wherein the contact between the first capstan belt and the first capstan pulley defines a first arc of contact and the first capstan belt defines a first belt width and a first belt thickness. The apparatus further includes a second capstan pulley defining a second outer diameter and a continuous second capstan belt under tension and in contact with the outer diameter of the second capstan pulley, wherein the contact between the second capstan belt and the second capstan pulley defines a second arc of contact and the second capstan belt defines a second belt width and a second belt thickness. The second arc of contact being at least 20° greater than the first arc of contact.

Another aspect of the present invention is to provide a method for proof testing an optical waveguide fiber including providing an optical fiber, drawing the fiber through a first rotating capstan with a first arc of contact, and drawing the fiber through a second rotating capstan with a second arc of contact that is at least 20° greater than the first arc of contact.

Additional features and advantages of the invention will be set forth in the detailed description which follows and will be apparent to those skilled in the art from the description or recognized by practicing the invention as described in the description which follows together with the claims and appended drawings.

It is to be understood that the foregoing description is exemplary of the invention only and is intended to provide an overview for the understanding of the nature and character of the invention as it is defined by the claims. The accompanying drawings are included to provide a further understanding of the invention and are incorporated and constitute part of this specification. The drawings illustrate various features and embodiments of the invention which, together with their description serve to explain the principals and operation of the invention.

DETAILED DESCRIPTION OF THE PREFERRED EMBODIMENT

Figure 1:
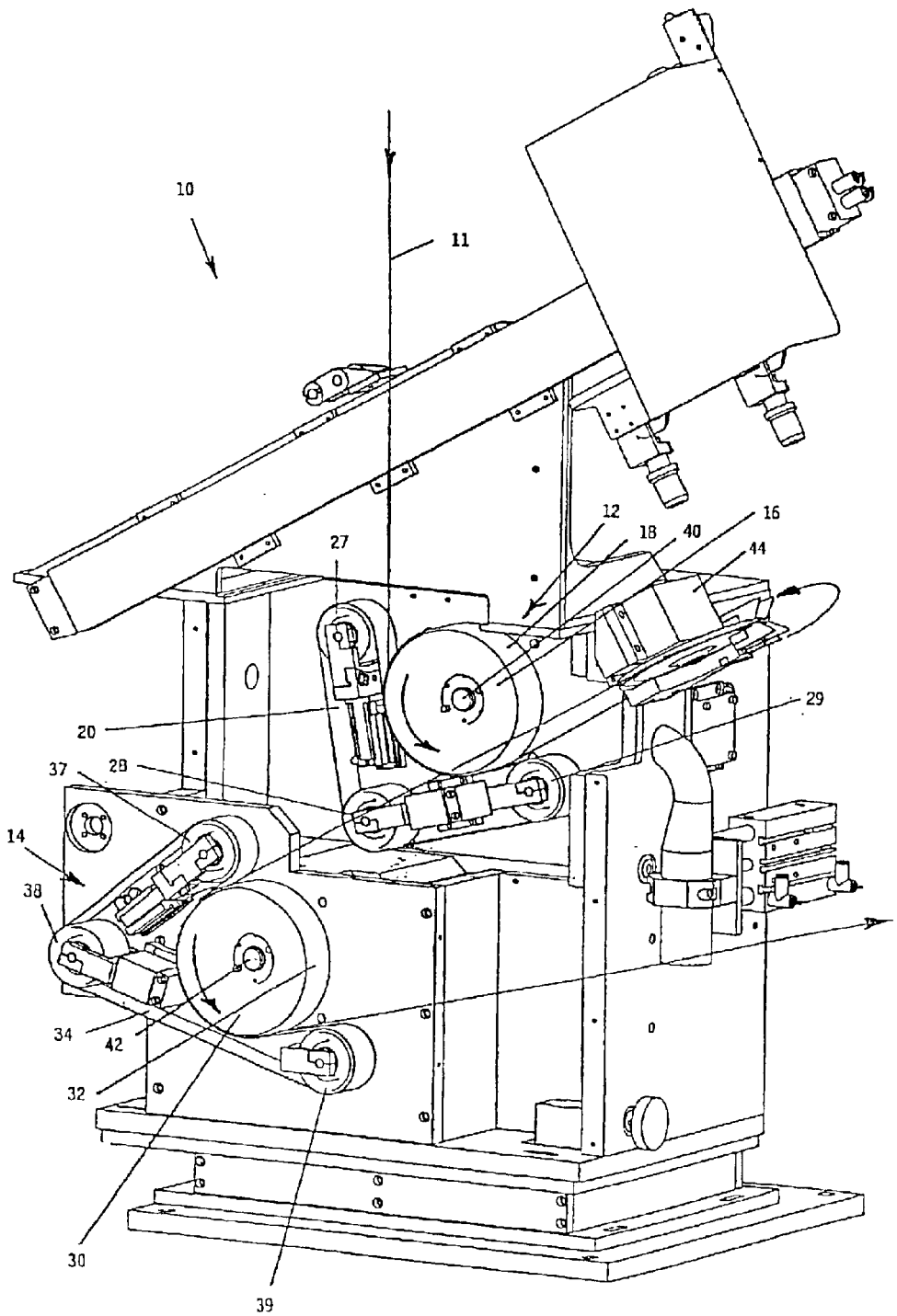
FIG. 1 is a perspective view of a draw machine including the capstans of the present invention.

For purposes of description herein, the terms "upper," "lower," "right," "left," "rear," "front," "vertical," "horizontal," and derivatives thereof shall relate to the invention as oriented in FIG. 1. However, it is to be understood that the invention may assume various alternative orientations and step sequences, except where expressly specified to the contrary. It is also to be understood that the specific devices and processes illustrated in the attached drawings and described in the following specification are exemplary embodiments of the inventive concepts defined in the appended claims. Hence, specific dimensions and other physical characteristics relating to the embodiments disclosed herein are not to be considered as limiting, unless the claims expressly state otherwise.

A draw machine 10 (FIG. 1) includes a first upper capstan assembly 12 and a second lower capstan assembly 14. Draw machine 10 is used for drawing an optical fiber 11 from a glass blank (not shown) that is hung within a draw tower (not shown), as well as for proof testing fiber 11. Draw machine 10 draws optical fiber 11 through a series of steps or processes within the draw tower, such as measuring the diameter of the optical fiber 11 as it is drawn from the glass blank, coating optical fiber 11, as well as treating the coating and measuring the diameter of the coating. Other operations may be conducted during the drawing process, but are unnecessary to the understanding of the present invention.

Figure 2:
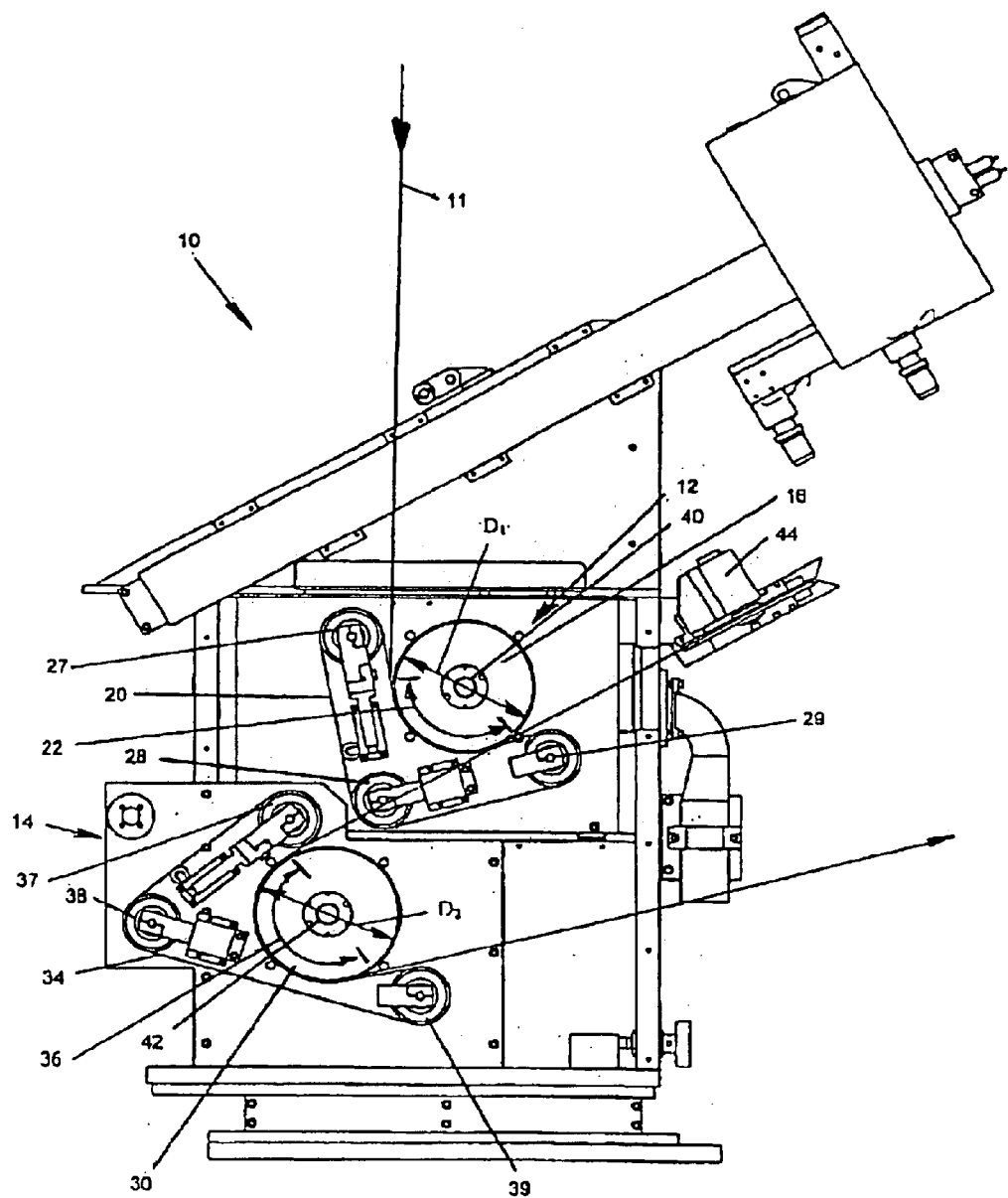
FIG. 2 is a front elevational view of the draw machine including the capstans of the present invention.

The first capstan assembly 12 of draw machine 10 includes a first capstan pulley 16 that has a first diameter $D_1$ with a first outer circumferential surface 18. First capstan assembly 12 further includes a continuous first capstan belt 20 that is under tension and in contact with first outer surface 18 of first capstan pulley 16. The contact between first capstan belt 20 and first capstan pulley 16 defines a first arc of contact 22 (FIG. 2). First capstan assembly 12 also includes a first set of at least three idler pulleys 27, 28, and 29 arranged around the periphery of capstan pulley 16 in spaced relationship thereto through an arc of about 180°. Stated differently, the idler pulley arc is defined as the arc of the capstans, 16 or 30, subtended by a line drawn through the centers of pulley 27 and 29 or pulleys 37 and 39, respectively. The arc is taken as that of the periphery of the capstan which is closest to the remaining idler pulley in the set of three idler pulleys. The periphery of idler pulleys 27, 28 and 29 can be adjusted by linear adjustments, described below, to provide the desired arc of contact 22 of belt 20 with pulley 16 as well as the tension on belt 20. The second capstan assembly 14 includes a second capstan pulley 30 with a diameter $D_2$ and a second outer circumferential surface 32. Second capstan assembly 14 further includes a continuous second capstan belt 34 that is held under tension and in contact with second outer surface 32 of second capstan pulley 30. The contact between second capstan belt 34 and second capstan pulley 30 defines a second arc of contact 36 (FIG. 2). Second capstan assembly 14 still further includes a second set of three idler pulleys 37, 38, and 39 arranged around the periphery of capstan pulley 30 in spaced relationship thereto through an arc of about 180°. The position of idler pulleys 37, 38 and 39 can be adjusted by linear adjustments, discussed below, to provide the desired arc of contact 36 of belt 34 with pulley 30 as well as the tension on belt 34. Idler pulleys 27, 28, and 29 of first capstan assembly 12 are positioned about first capstan pulley 16 such that the first arc of contact 22 is about 105° or greater. Idler pulleys 37, 38, and 39 of second capstan assembly 14 are positioned about second capstan pulley 30 such that the second arc of contact 36 is at least 20° greater than the first arc of contact. Preferably, the first arc of contact 22 is equal to or greater than about 105°, while the second arc of contact is equal to or greater than about 125°. Most preferably, the first arc of contact is 105° while the second arc of contact is 153°.

First capstan pulley 16 and second capstan pulley 30 are cylindrically shaped and are similarly dimensioned (i.e. $D_1=D_2$), and in one embodiment the diameters was about 6 inches. First outer surface 18 of first capstan pulley 16 and second outer surface 32 of second capstan pulley 30 are each constructed of hardened steel. First capstan pulley 16 is independently driven for rotational movement by a first capstan driveshaft 40, while second capstan pulley 30 is independently driven for rotational movement by a second driveshaft 42. Drive motors (not shown) are conventionally coupled to drive shafts 40 and 42 and coupled to a central controller to regulate the rotational speed of capstan pulleys 16 and 30.

Figure 3:
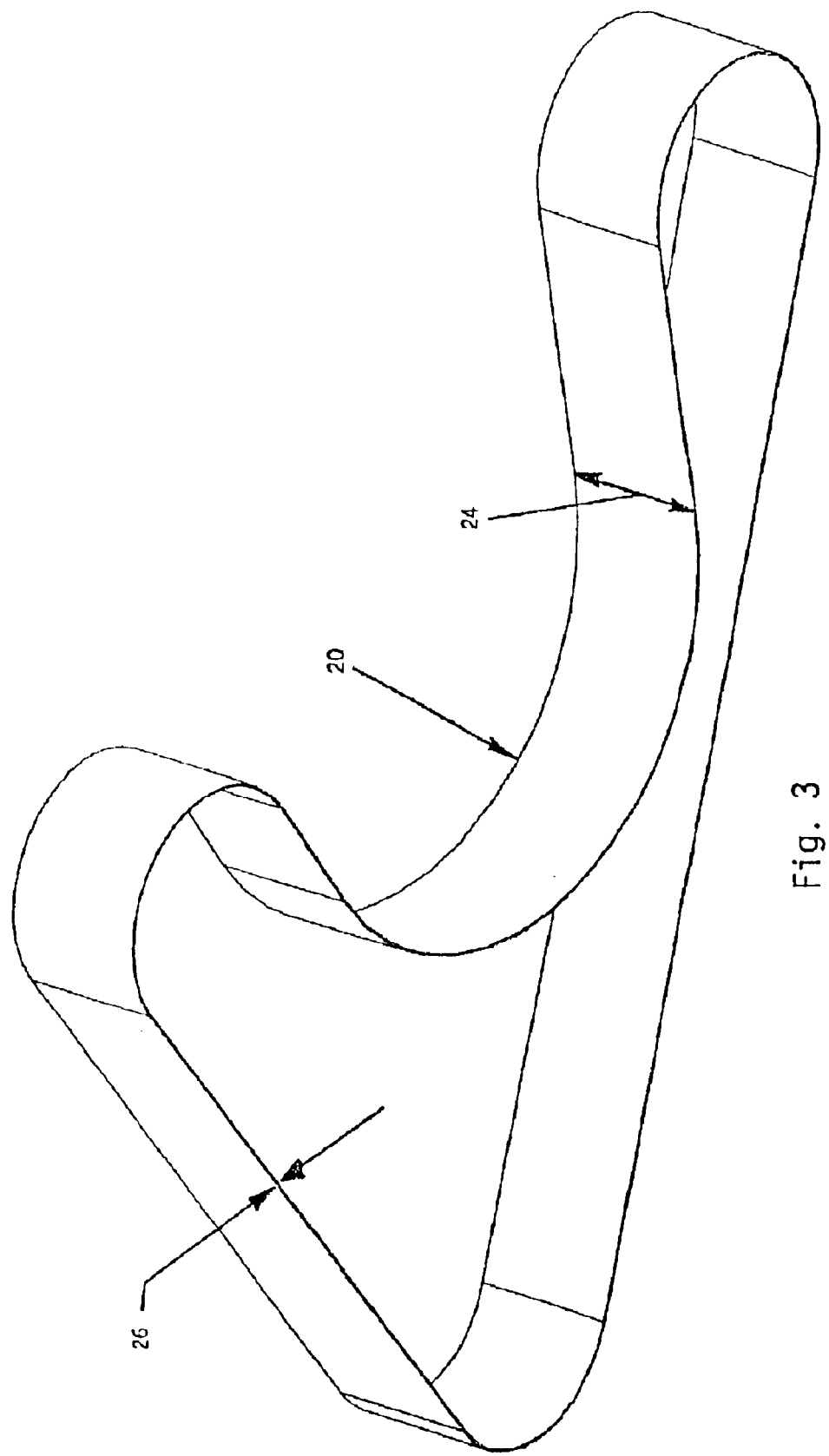
FIG. 3 is a perspective view of a capstan belt.

First capstan belt 20 and second capstan belt 34 are similar in construction, therefore a description of first belt 20 is illustrative of both first and second capstan belts 20 and 34, respectively. First capstan belt 20 (FIG. 3) is constructed of pliable fibrous material such as a polyester cord or mesh which is embedded with a material such as neoprene. It should be noted that other materials typically used in the industry for providing a sufficient coefficient of friction between first capstan belt 20 and optical fiber 11 may be substituted. First capstan belt 20 (FIG. 3) defines a width 24 and a thickness 26. Second capstan belt 34 has a second belt width and a second belt thickness, which are each similar to width 24 and thickness 26 of first capstan belt 20. The width 24 of first capstan belt 20 is preferably greater than or equal to 1.5 inches. First capstan belt thickness 26 is preferably less than 0.6 mm. More preferably, the width 24 of first capstan belt 20 is greater than or equal to 1.5 inches, while the thickness 26 of first capstan belt 20 is less than or equal to 0.59 mm. Most preferably, first capstan belt width 24 is equal to 1.5 inches, while first capstan belt thickness 26 is equal to 0.59 mm.

First capstan belt 20 and second capstan belt 34 are further each provided with a lateral modulus of elasticity and a longitudinal modulus of elasticity. Preferably, the lateral modulus of elasticity is between about 1/5 to about 1/6 the longitudinal modulus of elasticity.

The first set of at least three idler pulleys 27, 28, and 29 (FIG. 1) are encircled by first capstan belt 20 and are each in contact therewith, thereby creating a tension therein, which in one embodiment was between about 1.5 kg to about 2.5 kg. Idler pulley 27 is pneumatically adjustable, thereby allowing an operator to adjust the tension within first capstan belt 20. Similarly, the second set of at least three idler pulleys 37, 38, and 39 are encircled by second capstan belt 34 and are each in contact therewith, thereby creating a tension therein, which in one embodiment was between about 1.5 kg to about 2.5 kg. Idler pulley 37 is pneumatically adjustable, thereby allowing an operator to adjust the tension within second capstan belt 34. The adjustment mechanisms associated with pulleys 27 and 37 provide a constant tension within belts 20 and 34, respectively, and compensate for any changes in the rotational speed of the capstan pulleys 16 and 30 and any corresponding change in the lengths of belts 20 and 34. Idler pulleys 27 and 37 may be adjusted by pneumatic or hydraulic means, or any other means providing a constant force within belts 20 and 34. An advantage of the three pulleys spaced through an arc of about 180° (note the previous comments on this arc & the difference between the first and second capstans) around the capstan pulleys is that they ensure adequate belt tracking at low belt tensions, as discussed below, and allow for short belt "spans" of about 12 inches or less.

Another advantage of the three pulley system as is exemplified by first set of idler pulleys 27, 28, and 29, as well as second set of idler pulleys 37, 38, and 39, is the size in the arc of contact 22 between first capstan pulley 16 and first capstan belt 20 and between second capstan pulley 30 and second capstan belt 34, relative to those normally used in off-line proof testing machines, which typically incorporate arcs of contact of 90°. As discussed above, as the arc of slip increases, which results in a reduction of shear forces acting on optical fiber 11, the arc of adhesion decreases. Proof testing may become unstable if the arc of adhesion drops below 20°, and may be fatally compromised as the arc of adhesion approaches 0°. Increasing the total arc of contact 22 and 36 allows for a large slip region while maintaining an adequate arc of adhesion or non-slip region. First and second capstan assemblies 12 and 14 can reliably proof test optical fiber up to at least 200 kpsi.

In operation, optical fiber 11 is positioned between first capstan pulley 16 and first capstan belt 20. The tension in first capstan belt 20 generates a load between first capstan belt 20 and first capstan pulley 16 and causes first capstan belt 20 to deform about or drape over optical fiber 11. The friction generated between first capstan pulley 16, optical fiber 11 and first capstan belt 20 causes optical fiber 11 to be pulled or drawn from the glass blank as first capstan pulley is rotated by way of first driveshaft 40. Optical fiber 11 can then be routed to a plurality of other devices and processes 44. Optical fiber then is routed through the second capstan assembly 14. More specifically, optical fiber 11 is positioned between second capstan pulley 30 and second capstan belt 34. The tension in second capstan belt 34 generates a load between second capstan belt 34 and second capstan pulley 30 and causes second capstan belt 34 to deform about or drape over optical fiber 11. The friction generated between second capstan pulley 30, optical fiber 11 and second capstan belt 34 allows stress testing of optical fiber 11 as optical fiber 11 passes through first capstan assembly 12 and second capstan assembly 14. More specifically, the surface speed of the second capstan pulley 30 can be varied with respect to the surface speed of the first capstan pulley 16, thereby allowing for placement of a stressing load upon optical fiber 11 and the proof testing thereof.

First and second capstan belts 20 and 34 are significantly wider and thinner than typical capstan belts used in draw machines or during optical fiber proof testing processes. The increase of width 24 of first capstan belt 20 and the width of the second capstan belt 34 yields a net reduction in the proportion of the load generated between first capstan pulley 16 and first capstan belt 20 to be borne by optical fiber 11 as optical fiber 11 passes therebetween. The decrease in thickness of first and second capstan belts 20 and 34 results in a decrease of lateral stiffness of the belts 20 and 34 which results in a sufficient belt drape of belts 20 and 34 over optical fiber 11 even though the total load borne by fiber 11 is reduced as a result of the increase in total belt width. Belt tracking and lateral fixity of optical fiber 11, as it passes through first and second capstan assemblies 12 and 14, are determined by total belt load, or tension within the belts 20 and 34, and the amount of belt drape over fiber 11, whereas shear is determined only by the fraction of that load borne by fiber 11. As a result, decreasing the total load between capstan pulleys 16 and 30 and capstan belts 20 and 34 while reducing the lateral stiffness of belts 20 and 34 enables reduction in the load borne by fiber 11 while maintaining adequate tracking and lateral fixity.

As illustrated, the mismatch between the arc of contact 22 of first capstan assembly 12 and the arc of contact 36 of second capstan assembly 14 reduces the propensity for slip. First capstan assembly 12, as arranged, is a self-energizing system that acts against allowing slip to continue. More specifically, slip of optical fiber 11 through first capstan assembly 12 increases as either the tension in first capstan belt is lowered, or the ratio of outlet fiber tension to the inlet fiber tension increases. The fiber tension increases while the shear forces on the fiber also increase as the fiber 11 proceeds through first arc of contact 22 of first capstan assembly 12 because of the difference in surface speed between first capstan pulley 16 and second capstan pulley 30. As a result, the propensity for fiber 11 to slip increases as the fiber 11 proceeds through first arc of contact 22 of first capstan assembly 12. However, the lateral load as supported by fiber 11, i.e., the sum of the load on the fiber due to belt tension and the load on the fiber due to fiber tension, also increases as the fiber tension increases, thereby delaying the onset of slip. Therefore, the greater the fiber tension generated within first capstan assembly, the less the propensity for the slip to continue. Second capstan assembly 14 acts in opposite sense to first capstan assembly 12 in that the inlet fiber tension which is the same as the proof testing tension is greater than the outlet tension. The fiber tension decreases while the shear forces increase as fiber 11 proceeds through second arc of contact 36 of second capstan assembly 14. As a result, the propensity for fiber 11 to slip increases as fiber 11 proceeds through second arc of contact 36 of second capstan assembly 14. It should be noted that fiber 11 is subjected to decreasing fiber tension and consequently decreasing lateral load when proceeding through second arc of contact 36 than when proceeding through first arc of contact 22, thereby requiring second arc of contact 36 to be greater than first arc of contact 22 to balance the increasing shear forces through the arc of contact. By distributing the total arc of contact between capstan assemblies 12 and 14 in an unequal manner, the propensity for catastrophic slip of the total system is minimized.

The increase in belt width and the decrease in belt thickness coupled with the increased arc of contact provide for shear reduction of about 70% as compared with currently used processes while maintaining stable proof testing and good belt tracking and lateral fixity. The reduction in shear results in less stress being placed upon optical fiber 11 during the proof testing process, thus minimizing the possibility of damage to the coating of fiber 11.

In the foregoing description, it will be readily appreciated by those skilled in the art that modifications may be made to the invention without departing from the concepts disclosed herein. Such modifications are to be considered as included in the following claims, unless these claims by their language expressly state otherwise.

It will become apparent to those skilled in the art that various modifications to the preferred embodiment of the invention as described herein can be made without departing from the spirit or scope of the invention as defined by the appended claims.

The invention claimed is:

1. An apparatus for proof testing an optical waveguide fiber, comprising:
   a first capstan pulley defining a first outer diameter;
   a continuous first capstan belt under tension and in contact with said first outer diameter of said first capstan pulley, the contact between said first capstan belt and said first capstan pulley defining a first arc of contact, said first capstan belt defining a first belt width and a first belt thickness and a first belt length;
   a second capstan pulley defining a second outer diameter; and
   a continuous second capstan belt under tension and in contact with said second outer diameter of said second capstan pulley, the contact between said second capstan belt and said second capstan pulley defining a second arc of contact, said second capstan belt defining a second belt width, a second belt thickness and a second belt length;
   wherein said first arc of contact is equal to or greater than about 105° and said second arc of contact is at least 20° greater than said first arc of contact.

2. The apparatus described in claim 1, wherein said first width of said first capstan and belt said second width of said second capstan belt each have a lateral modulus of elasticity, and said first length of said first capstan and said second length of said second capstan belt each have a longitudinal modulus of elasticity, and wherein said lateral modulus of elasticity is between about 1/5 and about 1/6 of the longitudinal modulus elasticity.

3. The apparatus described in claim 2, wherein said first width of said first capstan belt and said second width of said second capstan belt are each equal to or greater than about 1.5 inches and said first thickness of said first capstan belt and said second thickness of said second capstan belt are each equal to or less than about 0.6 mm.

4. The apparatus described in claim 3, further including:
   a set of at least three idler pulleys encircled by said first capstan belt.

5. The apparatus described in claim 4, wherein said pulleys of said first set are spaced through an arc of about 180° around said first capstan pulley.

6. The apparatus described in claim 5, wherein at least one of said first set of idler pulleys is adjustable such that adjustment of said at least one of said first set of idler pulleys adjusts the tension in said first capstan belt.

7. The apparatus described in claim 6, further including:
   a second set of at least three idler pulleys encircled by said second capstan belt.

8. The apparatus described in claim 7, wherein said pulleys of said second set are spaced through an arc of about 180° around said second capstan pulley.

9. The apparatus described in claim 8, wherein at least one of said second set of idler pulleys is adjustable such that adjustment of said at least one of said second set of idler pulleys adjusts the tension in said second capstan belt.

10. The apparatus described in claim 1, further including:
    a set of at least three idler pulleys encircled by said first capstan belt.

11. The apparatus described in claim 10, wherein said pulleys of said first set are spaced through an arc of about 180° around said first capstan pulley.

12. The apparatus described in claim 10, wherein at least one of said first set of idler pulleys is adjustable such that adjustment of said at least one of said first set of idler pulleys adjusts the tension in said first capstan belt.

13. The apparatus described in claim 1, further including:
    a second set of at least three idler pulleys encircled by said second capstan belt.

14. The apparatus described in claim 13, wherein said pulleys of said second set are spaced through an arc of about 180° around said second capstan pulley.

15. The apparatus described in claim 13, wherein at least one of said second set of idler pulleys is adjustable such that adjustment of said at least one of said second set of idler pulleys adjusts the tension in said second capstan belt.

16. An apparatus for screen testing an optical waveguide fiber, comprising:
    a first capstan pulley defining a first outer diameter;
    a continuous first capstan belt under tension and in contact with said first outer diameter of said first capstan pulley, the contact between said first capstan belt and said first capstan pulley defining a first arc of contact, said first capstan belt defining a first width, a first thickness and a first belt length;
    a second capstan pulley defining a second outer diameter; and
    a continuous second capstan belt under tension and in contact with said second outer diameter of said second capstan pulley, the contact between said second capstan belt and said second capstan pulley defining a second arc of contact, said second capstan belt defining a second width, a second thickness and a second belt length;
    wherein said first width of said first capstan belt and said second width of said second capstan belt each have a lateral modulus of elasticity, and said first length of said first capstan belt and said second length of said second capstan belt each have a longitudinal modulus of elasticity, and wherein said lateral modulus of elasticity is between about 1/5 and about 1/6 of the longitudinal modulus of elasticity.

17. The apparatus described in claim 16, wherein said first width of said first capstan belt and said second width of said second capstan belt are each equal to or greater than about 1.5 inches and said first thickness of said first capstan belt and said second thickness of said second capstan belt are each equal to or less than about 0.6 mm.

18. The apparatus described in claim 17, further including:
   a set of at least three idler pulleys encircled by said first capstan belt.

19. The apparatus described in claim 18, wherein said pulleys of said first set are spaced through an arc of about 180° around said first capstan pulley.

20. The apparatus described in claim 19, wherein at least one of said first set of idler pulleys is adjustable such that adjustment of said at least one of said first set of idler pulleys adjusts the tension in said first capstan belt.

21. The apparatus described in claim 20, further including:
   a second set of at least three idler pulleys encircled by said second capstan belt.

22. The apparatus described in claim 21, wherein said pulleys of said second set are spaced through an arc of about 180° around said second capstan pulley.

23. The apparatus described in claim 22, wherein at least one of said second set of idler pulleys is adjustable such that adjustment of said at least one of said second set of idler pulleys adjusts the tension in said second capstan belt.

24. The apparatus described in claim 17, wherein said second arc of contact is at least 20° greater than said first arc of contact.

25. An apparatus for proof testing an optical fiber comprising:
   a first capstan pulley defining a first outer diameter;
   a continuous first capstan belt under tension and in contact with said first outer diameter of said first capstan pulley, the contact between said first capstan belt and said first capstan pulley defining a first arc of contact;
   a second capstan pulley defining a second outer diameter; and
   a continuous second capstan belt under tension and in contact with said second outer diameter of said second capstan pulley, the contact between said second capstan belt and said second capstan pulley defining a second arc of contact;
   wherein said second arc of contact is at least 20° greater than said first arc of contact.

26. The apparatus described in claim 25, wherein said first arc of contact is equal to or greater than 105°, and said second arc of contact is equal to or greater than 153°.

27. The apparatus described in claim 25, wherein said first capstan belt and said second capstan belt each have a width of equal to or greater than about 1.5 inches and a thickness of equal to or less than about 0.6 mm.

28. The apparatus described in claim 25, wherein said first width of said first capstan and said second width of said second capstan belt each have a lateral modulus of elasticity, and said first length of said first capstan and said second length of said second capstan belt each have a longitudinal modulus of elasticity, and wherein said lateral modulus of elasticity is between about $\frac{1}{5}$ and about $\frac{1}{6}$ of the longitudinal modulus elasticity.

29. The apparatus described in claim 25, further including:
   a set of at least three idler pulleys encircled by said first capstan belt.

30. The apparatus described in claim 29, wherein at least one of said first set of idler pulleys is adjustable such that adjustment of said at least one of said first set of idler pulleys adjusts the tension in said first capstan belt.

31. The apparatus described in claim 29, wherein said pulleys of said first set are spaced through an arc of about 180° around said first capstan pulley.

32. The apparatus described in claim 29, further including:
   a second set of at least three idler pulleys encircled by said second capstan belt.

33. The apparatus described in claim 32, wherein at least one of said second set of idler pulleys is adjustable such that adjustment of said at least one of said second set of idler pulleys adjusts the tension in said second capstan belt.

34. The apparatus described in claim 32, wherein said pulleys of said second set are spaced through an arc of about 180° around said second capstan pulley.

35. A method for proof testing an optical waveguide fiber, said method comprising:
   providing an optical fiber;
   drawing the fiber between a first rotating capstan and a first capstan belt through a first arc of contact; and
   drawing the fiber between a second rotating capstan and a second capstan belt through a second arc of contact that is at least 20° greater than the first arc of contact wherein the arc of contact is defined as an arc through which the respective belt contacts the outer circumference of the corresponding rotating capstan.

36. The method described in claim 35, further including:
   testing the proof strength of the optical fiber by rotating the second capstan to obtain a faster surface speed than that of the first capstan.

37. The method described in claim 35, wherein said drawing steps include employing capstan belts with a width equal to or greater than about 1.5 inches.

38. The method described in claim 35, wherein said drawing steps include employing capstan belts with a thickness equal to or less than 0.6 mm.

39. The method described in claim 35, wherein said drawing steps include employing capstan belts that have a lateral modulus of elasticity that is between about $\frac{1}{5}$ and $\frac{1}{6}$ the longitudinal modulus of elasticity of the capstan belts.

* * * * *